United States Patent [19]

Bernhardt et al.

[11] Patent Number: 5,232,690
[45] Date of Patent: Aug. 3, 1993

[54] USE OF ZINC CALCIUM HYDROXIDE, LECITHIN AND PAO AS AN ADJUVANT FOR ANTIGEN SOLUTIONS, AND ANTIGEN SOLUTIONS TREATED WITH AN ADJUVANT OF THIS TYPE

[75] Inventors: Dieter Bernhardt, Cölbe; Joachim Hilfenhaus, Marburg, both of Fed. Rep. of Germany

[73] Assignee: Behringwerke Aktiengesellschaft, Marburg, Fed. Rep. of Germany

[21] Appl. No.: 665,477

[22] Filed: Mar. 6, 1991

[30] Foreign Application Priority Data

Mar. 8, 1990 [DE] Fed. Rep. of Germany ....... 4007315

[51] Int. Cl.$^5$ .............................................. A61K 39/00
[52] U.S. Cl. ........................................ 424/88; 424/89; 424/92; 424/643; 424/722; 514/114; 514/762
[58] Field of Search ............... 424/88, 89, 92, 643, 424/722; 514/114, 762

[56] References Cited

U.S. PATENT DOCUMENTS

| | | | |
|---|---|---|---|
| 4,053,585 | 10/1977 | Allison et al. | 424/92 |
| 4,698,221 | 10/1987 | Straub | 424/89 |
| 4,803,070 | 2/1989 | Cantrell et al. | 424/92 |
| 4,806,352 | 2/1989 | Cantrell | 424/92 |

FOREIGN PATENT DOCUMENTS

| | | |
|---|---|---|
| 0108316A2 | 5/1984 | European Pat. Off. . |
| 0343548A2 | 11/1989 | European Pat. Off. . |
| 0363835A1 | 4/1990 | European Pat. Off. . |

*Primary Examiner*—Jeffrey E. Russel
*Assistant Examiner*—P. Lynn Touzeau
*Attorney, Agent, or Firm*—Finnegan, Henderson, Farabow, Garrett & Dunner

[57] ABSTRACT

A process for treating antigen solutions with an adjuvant is described, in which process a zinc hydroxide/calcium hydroxide gel and, where appropriate, additionally a lecithin and, where appropriate, additionally a polyalphaolefin is added to the antigen solution.

7 Claims, No Drawings

USE OF ZINC CALCIUM HYDROXIDE, LECITHIN AND PAO AS AN ADJUVANT FOR ANTIGEN SOLUTIONS, AND ANTIGEN SOLUTIONS TREATED WITH AN ADJUVANT OF THIS TYPE

The invention relates to the use of zinc calcium hydroxide, lecithin and PAO as an adjuvant for antigen solutions and to antigen solutions treated with an adjuvant of this type.

Many antigens show so little immunogenicity that, after a single injection into an animal, they trigger off only a weak immune response or none that can be detected. To amplify the immune response of the body to an antigenic stimulus adjuvants are therefore added to the antigen. Most of the inactivated viral and bacterial vaccines for this season contain adjuvants. In these viral and bacterial vaccines predominantly $Al(OH)_3$ and $ALPO_4$, individually or in combination, vegetable oils or mineral oils obtained from crude oil fractions, so-called medical pharmaceutical white oils of a not exactly defined composition are used. Freund's complete and incomplete adjuvant containing $^R$Bayol F mineral oil with and without mycobacterial extract is predominantly used in experimental vaccines.

However, in addition to local reactions, these adjuvants can also have systemic side effects.

In addition to the local and general tolerance of adjuvants the following are of interest:

1. Their immunological mechanisms of action, i.e. the action induced by them;
2. Their pharmacokinetics (biodegradability).

As regards 1, it is generally known that the mineral adjuvants ($Al(OH)_3$, $ALPO_4$) predominantly only induce a humoral immune response while cellular immunity which plays a dominant role in many viral infections is only slightly stimulated or not at all.

The mineral oils and, in particular, Freund's adjuvant have different characteristics and, as is known, stimulate both the cellular and the humoral immune response.

As regards 2, the adjuvants which have been customary so far remain mainly at the injection site or are transported off and concentrated in other organs of the body where they have their immunological and possibly toxic effect, i.e. a degradation and an elimination only occurs after very long delay or not at all.

The components of the adjuvant according to the invention, namely zinc hydroxide/calcium hydroxide gel and lecithin, have different characteristics. They are metabolized in the body and are therefore less toxic.

In EP-A-0,108,316 (German Offenlegungsschrift 3,241,113) it was proposed to use zinc compounds, i.e. zinc salts, in addition to other substances as additives to vaccines.

EP-A-0,343,548 discloses polyalphaolefins (PAO) as adjuvants and EP Application 89 118565494 discloses zinc hydroxide gel and lecithin.

Surprisingly however, it has now been found that zinc hydroxide/calcium hydroxide gels, lecithin and PAO can be combined to an adjuvant which has the following properties:

1. The combined adjuvant has a markedly improved stimulating effect on the immune system in comparison with each of the 4 individual components which are effective as an adjuvant.
2. Surprisingly, the combined adjuvant has an improved general and local tolerance in comparison with zinc hydroxide gel and lecithin or PAO.

Description of the preparation process of zinc hydroxide/calcium hydroxide gel and lecithin 99 suspension by methods known per se:

Zinc hydroxide/calcium hydroxide gel:

1. Starting from $ZnCL_2$ and $CaCl_2 \times 2H_2O$, preparation of a 0.1 M solution in distilled water (0.1 mol/l in each case);
2. Sterilization of the Zn Ca salt solution by filtration (0.2 $\mu$ membrane filter);
3. A base, preferably 10 N NaOH or 10 N KOH, is added under sterile conditions and while stirring until a pH of 6.8–7.8 is reached;
4. The precipitated zinc hydroxide/calcium hydroxide gel can preferably be homogenized by $^R$Ultraturax treatment.

These ZnCa salts used as starting material here are only examples. It is also possible to prepare a zinc hydroxide/calcium hydroxide gel directly in an antigen suspension while monitoring the pH. If the Zn Ca salt solutions used are not sterile, but the work is carried out under sterile conditions, the gel can be autoclaved at 120° C. for 20 min.

Preparation of a 20% lecithin 99 suspension:

1. 20 g of lecithin are suspended in 100 ml of PBS (phosphate-buffered salt solution according to Dulbecco), pH 7.2;
2. Autoclaving of the suspension at 120° C. for 20 min;
3. After cooling, the suspension is homogenized;
4. The pH of the suspension is adjusted to 7.0–7.8 using 10 N NaOH.

Exemplary preparation of an adjuvant combination (BW 89) according to the invention:

| | |
|---|---|
| PAO | 26.67% |
| are thoroughly mixed with ®Tween 81 and | 6.00% |
| ®Tween 80 | 2.00% |
| (both are polyoxyethylene sorbitan monoesters) by means of a homogenizer. | |
| While mixing using ®Ultraturax, 0.1M zinc calcium hydroxide gel | 50.00% |
| and a 20% suspension of lecithin 99 are added | 15.33% |
| | 100.00% |

The adjuvant combination obtained in this way may be added to an antigen in any percentage desired.

The lecithin is preferably added as a 20% suspension. 1–10%, preferably 5%, of a suspension of this type can be added.

The polyalphaolefin is added to a concentration of 1–40%, preferably 10%.

A different possibility of preparing the adjuvant combination is:

1. The addition of zinc calcium hydroxide gel and lecithin 99 suspension to the antigen and
2. The preparation of the W/O emulsion (water-in-oil emulsion) with PAO, Tween 81 and 80 and the antigen/adjuvant mixture described under 1.

However, an adjuvant combination according to the invention can also be prepared in the following way, with all operation steps being carried out under sterile conditions:

| | |
|---|---|
| 1. PAO | 26.67% |
| ®Tween 80 | 6.00% |
| ®Tween 81 | 2.00% |
| are thoroughly mixed by means of | |

-continued

| | |
|---|---|
| Ultraturax. | |
| 2. A water-in-oil (W/O) emulsion is prepared by adding a sterile 0.1M solution of ZnCl$_2$/CaCl$_2$, and mixing by means of ®Ultraturax. | 50.00% |
| 3. While monitoring the pH (6.5–7.5), zinc calcium hydroxide gel is precipitated in the W/O emulsion by adding 10N NaOH while mixing using the Ultraturax. | |
| 4. Then, while mixing, 20% lecithin 99 is added | 15.33% |
| Total | 100.00% |

Another possibility of preparing the adjuvant combination is:

1. Adding zinc calcium hydroxide gel and lecithin 99 suspension to the antigen and allowing the antigen to adsorb and
2. Preparing the W/O emulsion with PAO, $^R$Tween 81 and 80 and the antigen/adjuvant mixture mentioned under 1.

The following examples illustrate the advantages of the adjuvant combination according to the invention:

EXAMPLE 1

Aujeszky disease virus (AV) was multiplied in primary pig kidney cell cultures. Once 100% of the cultures had been destroyed virus-specifically, i.e. waiting until the cells were completely destroyed (CPE), the virus was harvested and purified by centrifugation and filtration. Then, the AV was inactivated using ethyleneimine. After sterility and safety had been checked, four vaccines were prepared from this inactivated AV antigen.

The composition of the vaccine is listed in Table 1 below (data in ml):

| | Vaccine | | | |
|---|---|---|---|---|
| Adjuvant/antigen | A | B | C | D |
| 2% Al(OH)$_3$ | 20 | | | |
| 0.1M Zn(OH)$_2$ | | 17 | | |
| 20% lecithin 99 | | 3 | | |
| PAO | | | 20 | |
| BW 89 adjuvant combination | | | | 20 |
| AV antigen | 80 | 80 | 80 | 80 |
| Total | 100 | 100 | 100 | 100 |

In order to determine the local tolerance, 2 guinea-pigs weighing 450 g were inoculated interplantarly with each vaccine with 0.1 ml in each case.

After the inoculation, the plantae of the guinea-pig were examined daily for reddening, swelling and other visible pathological anatomical changes for 4 weeks to assess the local tolerance, and a value of intolerance was determined in points. The more serious the visible pathological anatomical changes are, the more points in the value and the greater the intolerance.

The intolerance points determined are listed in the form of a table below:

| | Vaccine | | | |
|---|---|---|---|---|
| | A | B | C | D |
| Intolerance points animal 1 | 245 | 122.5 | 42.5 | 2.5 |
| Intolerance points animal 2 | 257 | 187.5 | 82.5 | 2.5 |

-continued

| | Vaccine | | | |
|---|---|---|---|---|
| | A | B | C | D |
| Total intolerance points | 502 | 310.0 | 125.0 | 5.0 |

As can be seen from the results in the table, the BW 99 adjuvant combination (vaccine D) is by far superior to all the other adjuvants with regard to local tolerance.

In order to assess the efficacy of the vaccines, blood was taken from the guinea-pigs 4 weeks after the vaccination and the neutralizing antibodies in the serum against the AV were determined.

The neutralization titers determined are listed in the form of a table below:

| | Vaccine | | | |
|---|---|---|---|---|
| Animal | A | B | C | D |
| Animal 1 | <2 | 1:6 | 1:10 | 1:21 |
| Animal 2 | <2 | 1:8 | 1:12 | 1:24 |

As is shown by the results in this table, the efficacy of the adjuvant combination (vaccine D) is better than that of the other adjuvants.

DETERMINATION OF THE GENERAL TOLERANCE

10 NMRI mice, in each case, weighing 30 g were vaccinated subcutaneously with 0.3 ml, in each case, of the vaccines which had been prepared as described above.

To determine the general tolerance, the weight of the animals were monitored daily up to 8 days after vaccination.

The weight increase in the animals was

| | |
|---|---|
| 11 g | with vaccine A |
| 6 g | with vaccine B |
| 8 g | with vaccine C |
| 11 g | with vaccine D |
| 10 g | in untreated controls. |

The increase in weight clearly shows that the BW 89 adjuvant combination has good general tolerance.

EXAMPLE 2

PI$_3$ virus (parainfluenza 3 virus) was multiplied in DBK cells. Once 80–100% of the cell lawn of the cultures had been virus-specifically destroyed, the virus was harvested and purified by means of centrifugation. After this the viral antigen was inactivated using ethyleneimine. A sterility and safety check was carried out and two vaccines were then prepared from the inactivated antigen.

Vaccine A contained (the percentages for the vaccine compositions are to be read as v:v):

| | |
|---|---|
| PI$_3$V antigen | 80.0% |
| 2% strength Al(OH)$_3$ | 19.5% |
| 10% strength saponin, Merck | 0.5% |

Vaccine B contained:

| | | |
|---|---|---|
| PI$_3$V antigen | 80.0% | |
| BW 89 | 20.0% | |

3 sheep in each case were vaccinated subcutaneously with 2.0 ml of either vaccine and revaccinated 4 weeks after vaccination using the same dosage. In order to check the local tolerance of the vaccines, the injection site was examined for swellings, reddenings, consistency and sensitivity.

With vaccine A, even 8 weeks after vaccination a post-vaccinal lump was visible, whose retrogression would, because of its firm consistency, still require several weeks. An essentially better local tolerance was shown by vaccine B. Between 14 and 21 days after vaccination a post-vaccinal lump at the injection site was no longer visible or palpable. None of the animals inoculated with vaccine A or B exhibited any disturbances in their general well-being.

EXAMPLE 3

To test the tolerance two blank vaccines (blank vaccines do not contain any antigen; in place of the antigen Eagles 59 medium is added. However the content of adjuvant is the same as provided for the vaccines) with the composition below were prepared;

Vaccine A contained:

| | |
|---|---|
| EB (physiological salt solution + vitamins + amino acids) | 90.0% |
| 2% strength Al(OH)$_3$ | 10.0% |

Vaccine B contained:

| | |
|---|---|
| EB | 90.0% |
| BW 89 | 10.0% |

3 horses were inoculated with vaccine A, and 6 horses with vaccine B using 2.0 ml subcutaneously.

A daily examination of the animals for local reactions was carried out for 8 days. The results are summarized in the form of a table below.

Local reactions in horses after vaccination with blank vaccines containing Al(OH)$_3$ or BW 89

| Animal No. | Vaccine | Local reactions in days after vaccination | | | | | | | |
|---|---|---|---|---|---|---|---|---|---|
| | | 1 | 2 | 3 | 4 | 5 | 6 | 7 | 8 |
| 1 | A | C | D | D | C | C | C | C | C |
| 2 | | C | C | D | D | D | D | C | C |
| 3 | | C | D | D | D | C | C | C | C |
| 4 | B | O | O | O | O | O | O | O | O |
| 5 | | O | O | O | O | O | O | O | O |
| 6 | | A | A | B | O | O | O | O | O |
| 7 | | A | A | O | O | O | O | O | O |
| 8 | | C | O | O | O | O | O | O | O |
| 9 | | C | O | O | O | O | O | O | O |

Size of swelling:
O = invisible, impalpable
A = pea sized
B = hazelnut sized
C = walnut sized
D = chicken egg sized As can be seen from this table, BW 89 is substantially better tolerated locally than Al(OH)$_3$. There was no considerable general reaction in any of the animals.

We claim:

1. A process for preparing an antigen solution for administration in vivo to effect immunization which comprises adding zinc hydroxide/calcium hydroxide gel, lecithin and polyalphaolefin to an antigen solution.

2. An adjuvant composition comprising an immunologically effective amount of zinc hydroxide/calcium hydroxide gel lecithin and polyalphaolefin.

3. A composition for administration in vivo to effect immunization comprising an immunologically effective amount of an antigen and an immunologically effective adjuvant composition as claimed in claim 2.

4. A composition as claimed in claim 3 further comprising 1–10%, of a 20% lecithin suspension.

5. A composition as claimed in claim 4 wherein the proportion of said 20% lecithin suspension is 5%.

6. A composition as claimed in claim 3 further comprising 1–40%, of a polyalphaolefin.

7. A composition as claimed in claim 6 wherein the proportion of said polyalphaolefin is 10%.

* * * * *

UNITED STATES PATENT AND TRADEMARK OFFICE
CERTIFICATE OF CORRECTION

PATENT NO. : 5,232,690
DATED : August 03, 1993
INVENTOR(S) : Dieter Bernhardt et al.

It is certified that error appears in the above-indentified patent and that said Letters Patent is hereby corrected as shown below:

Claim 2, column 6, line 32, after "gel" insert --,--.

Claim 4, column 6, line 38, after "1-10%" delete --,--.

Claim 6, column 6, line 42, after "1-40%" delete --,--.

Signed and Sealed this

Twenty-first Day of June, 1994

Attest:

BRUCE LEHMAN

*Attesting Officer*      Commissioner of Patents and Trademarks